United States Patent [19]

Hasse et al.

[11] Patent Number: 5,575,782
[45] Date of Patent: Nov. 19, 1996

[54] GARMENT-LIKE DISPOSABLE ABSORBENT ARTICLE HAVING A BLOUSED OUTER COVER

[75] Inventors: Margaret H. Hasse, Wyoming; Patrick J. Allen, Cincinnati, both of Ohio

[73] Assignee: The Procter & Gamble Company, Cincinnati, Ohio

[21] Appl. No.: 176,055

[22] Filed: Jan. 3, 1994

[51] Int. Cl.$^6$ ..................................................... A61F 13/15
[52] U.S. Cl. .......................... 604/385.1; 604/394; 604/396
[58] Field of Search .................................. 604/358, 385.1, 604/385.2, 378, 393, 394, 386, 387, 396

[56] References Cited

U.S. PATENT DOCUMENTS

| | | |
|---|---|---|
| 1,329,119 | 1/1920 | George . |
| 1,595,051 | 8/1926 | George . |
| 1,695,109 | 7/1927 | Kosloff . |
| 2,252,992 | 9/1940 | Steiner . |
| 2,523,079 | 9/1950 | Walter et al. . |
| 2,555,434 | 6/1951 | Anderson . |
| 2,594,229 | 4/1952 | Snyder et al. . |
| 3,237,625 | 10/1964 | Johnson . |
| 3,599,640 | 8/1971 | Larson . |
| 3,842,837 | 10/1974 | Sward . |
| 4,205,679 | 6/1980 | Repke et al. . |
| 4,249,532 | 2/1981 | Polansky et al. ............... 604/385.1 X |
| 4,341,216 | 7/1982 | Obenour .................................. 604/383 |
| 4,355,425 | 10/1982 | Jones et al. . |
| 4,496,360 | 1/1985 | Joffe et al. . |
| 4,610,680 | 9/1986 | LaFleur . |
| 4,610,681 | 9/1986 | Strohbeen et al. . |
| 4,619,649 | 10/1986 | Roberts . |
| 4,641,381 | 2/1987 | Heran et al. . |
| 4,646,362 | 3/1987 | Heran et al. . |
| 4,662,874 | 5/1987 | Korpman . |
| 4,671,793 | 6/1987 | Hults et al. . |
| 4,795,510 | 1/1989 | Wittrock et al. ........................ 156/64 |
| 4,935,021 | 6/1990 | Huffman et al. ..................... 604/385.1 |
| 4,938,753 | 7/1990 | Van Gompel et al. . |
| 4,938,757 | 7/1990 | Van Gompel et al. . |
| 4,940,464 | 7/1990 | Van Gompel et al. . |
| 5,032,120 | 7/1991 | Freeland et al. . |
| 5,087,253 | 2/1992 | Cooper . |
| 5,087,255 | 2/1992 | Sims . |
| 5,106,382 | 4/1992 | Henry . |
| 5,151,092 | 9/1992 | Buell et al. . |
| 5,171,239 | 12/1992 | Igaue et al. . |
| 5,185,011 | 2/1993 | Strasser . |
| 5,188,627 | 2/1993 | Igaue et al. . |
| 5,236,430 | 8/1993 | Bridges . |
| 5,246,433 | 9/1993 | Hasse et al. . |
| 5,275,590 | 1/1994 | Huffman et al. ..................... 604/385.2 |
| 5,458,590 | 10/1995 | Schleinz et al. ..................... 604/385.1 |

FOREIGN PATENT DOCUMENTS

| | | |
|---|---|---|
| 0477802A1 | 4/1992 | European Pat. Off. . |
| 0526868A2 | 2/1993 | European Pat. Off. . |
| 0547497 | 6/1993 | European Pat. Off. ............ 604/385.2 |
| 91-335616/46 | 1/1990 | Japan . |
| 364845/1992 | 12/1992 | Japan . |
| 2244909 | 12/1991 | United Kingdom . |

*Primary Examiner*—Debra S. Brittingham
*Assistant Examiner*—Mark O. Polutta
*Attorney, Agent, or Firm*—Steven W. Miller; E. Kelly Linman; Jacobus C. Rasser

[57] ABSTRACT

A disposable absorbent article for wearing about a wearer's lower torso is provided. The disposable absorbent article comprises: a chassis; an absorbent assembly joined to the chassis; and seams joining the front portion of the chassis to the rear portion of the chassis so as to form two leg openings and a waist opening. The garment comprises an outer layer having at least a portion of its periphery joined to at least a portion of the periphery of the inner layer of the chassis so that the outer layer can blouse away from the central area at selected portions. The bloused outer layer has a pattern imprinted thereon such that the inner layer with the absorbent assembly joined thereto is substantially unnoticeable to a viewer thereby providing a very garment like appearance to the absorbent article.

10 Claims, 3 Drawing Sheets

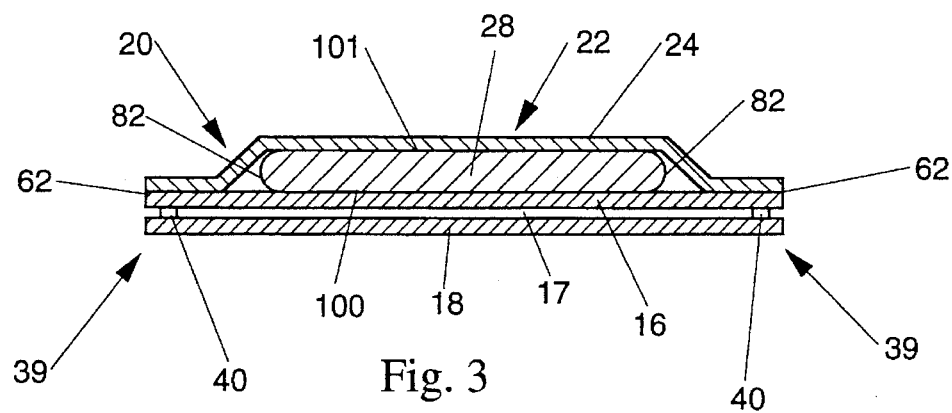
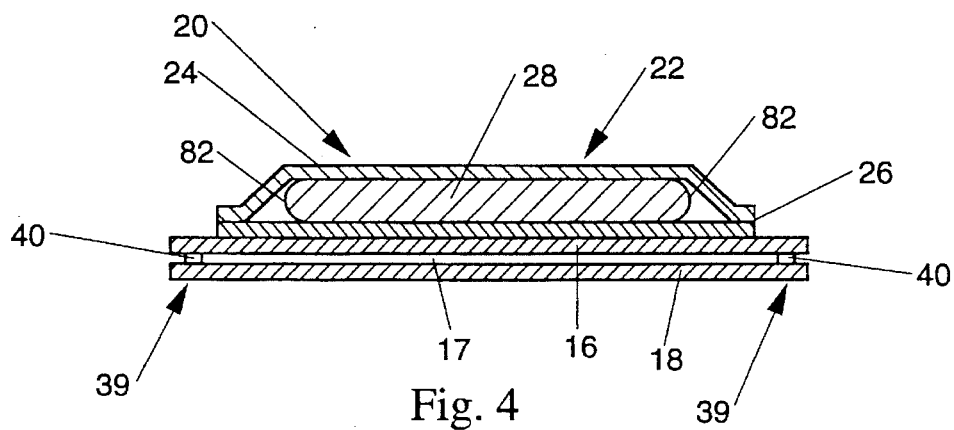
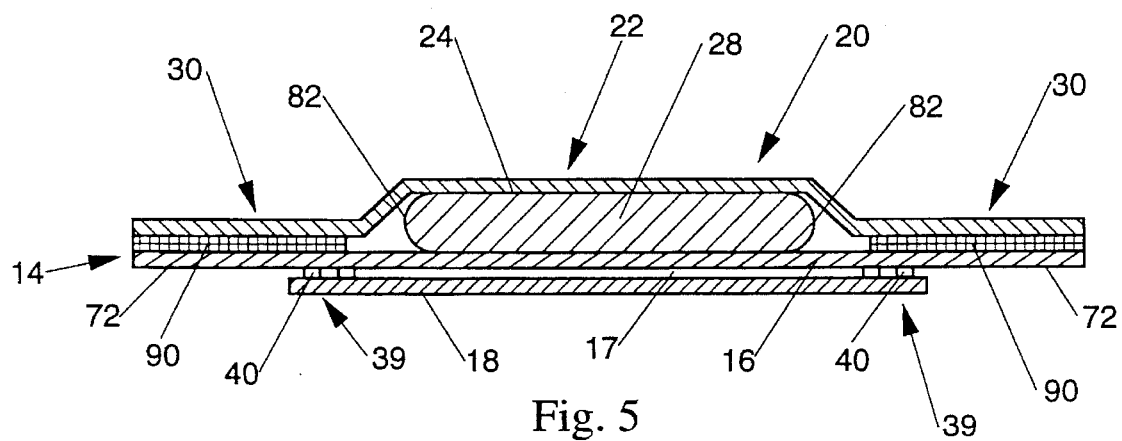

GARMENT-LIKE DISPOSABLE ABSORBENT ARTICLE HAVING A BLOUSED OUTER COVER

FIELD OF THE INVENTION

The present invention relates to disposable absorbent articles such as baby diapers, children's training pants, adult incontinence garments, and the like. The present invention relates more particularly to disposable absorbent articles having fixed sides, such as disposable training pants, which are placed in position on the wearer by inserting the wearer's legs into the leg openings and sliding the disposable absorbent article into position about the wearer's lower torso.

BACKGROUND OF THE INVENTION

Infants, children, and other incontinent individuals wear disposable absorbent articles to receive and contain urine and other bodily exudates. It has become increasingly important for disposable absorbent articles to be more garment-like in appearance. Absorbent articles having fixed sides, such as disposable training pants for use on toilet training children, have become popular for use on toilet-training children. It is particularly desirable that disposable training pants be very garment-like in appearance and feel so a toilet training child will distinguish it from a diaper, will want not to soil them, and will more easily adjust to cloth undergarments.

Absorbent articles, generally comprise a liquid impervious thermoplastic backsheet, a liquid pervious topsheet, an absorbent structure for absorbing bodily exudates, and elastic legbands and waistbands to gather the article for fit and containment. The absorbent structure, elastic legbands, and elastic waistbands are generally positioned between the topsheet and the backsheet, and usually adhesively secured thereto. This general structure is substantially liquid impervious, but is plastic in feel and resembles an absorbent article as a result of the absorbent core or outline of the absorbent core being visible through the backsheet.

Several structures have been developed to eliminate, as much as possible, the feel of plastic and appearance of an absorbent article. One such structure utilizes a backsheet comprising a film-coated nonwoven. This backsheet comprises a thermoplastic film that is extruded onto a nonwoven web. The heat of the film and the pressure applied during the process provides the adhesion between the film and nonwoven layer. While the film does help to maintain the integrity of the nonwoven layer, it also results in a stiffer and less desirable backsheet.

Another structure utilizes a backsheet comprising a thermoplastic film laminated to a nonwoven layer. The laminating is provided by applying an adhesive to the film or the nonwoven layer, and then attaching it to the other layers of the article. Thus, in both this second design and the first one mentioned above, the thermoplastic film and the nonwoven layer are joined totally along their mutually facing surfaces and the absorbent core or outline thereof is still visible through the backsheet.

Another structure utilizes a backsheet comprising an outer layer and inner layer which are intermittently or partially joined together. Such a structure is more garment-like in appearance and feel. However, the absorbent core is generally secured to the inner layer and is generally still visible through the outer layer 18 of the chassis. This is particularly true if there is a pattern or design printed on the inner layer.

It is, therefore, an object of the present invention to provide an absorbent article having a backsheet comprising an inner layer intermittently or partially joined to an outer layer which provides a garment-like appearance and feel and which substantially masks or hides the absorbent core or outline of the absorbent core from the viewer.

SUMMARY OF THE INVENTION

A disposable absorbent article for wearing about a wearer's lower torso is provided. The disposable absorbent article comprises: a chassis; an absorbent assembly joined to the chassis; and seams joining the front portion of the chassis to the rear portion of the chassis so as to form two leg openings and a waist opening. The chassis comprises. The bloused outer layer has a pattern imprinted thereon such that the inner layer with the absorbent assembly joined thereto is substantially unnoticeable to a viewer thereby providing a very garment like appearance to the absorbent article.

BRIEF DESCRIPTION OF THE DRAWING

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 3 is a cross-sectional view of the chassis shown in FIG. 2 taken along section line 3—3 of FIG. 2.

FIG. 4 is a cross-sectional view of an alternate embodiment of the present invention, wherein the absorbent assembly is an insert joined to the inner layer of the chassis.

FIG. 5 is a cross-sectional view of another alternate embodiment of the present invention, wherein the earflaps of the absorbent article are elasticized.

DETAILED DESCRIPTION OF THE INVENTION

Figure 1:
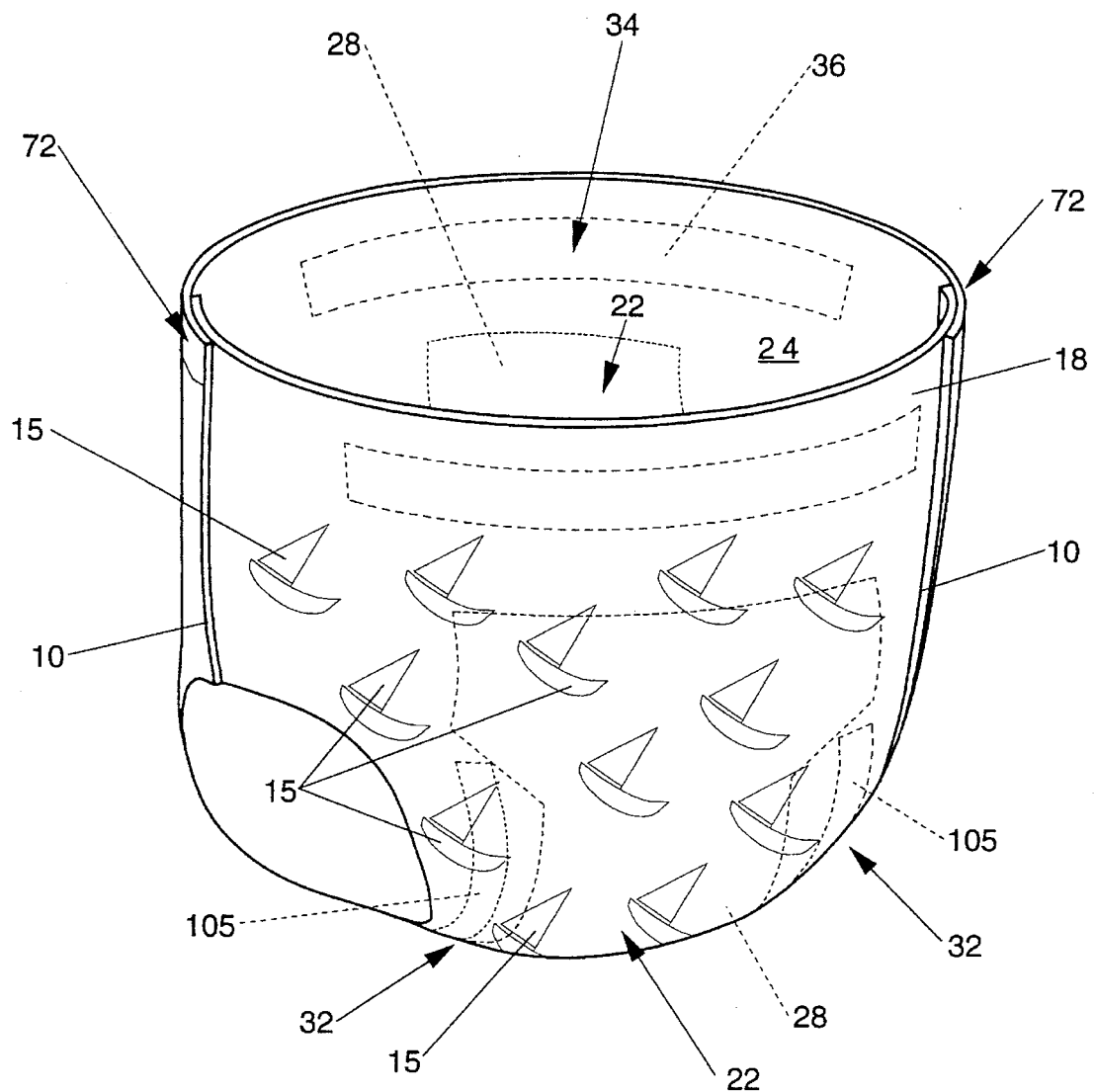
FIG. 1 is a perspective view of the disposable training pant embodiment of the present invention in a typical in-use configuration as it would be applied to a wearer.

Referring to the drawings, it will be noted that FIG. 1 is a perspective view of a disposable absorbent article in its typical in-use configuration. A disposable absorbent article is one which is intended to be discarded after it is used (i.e., it is not intended to be laundered or otherwise restored or reused). The disposable absorbent article is provided with an absorbent assembly which is placed in close proximity to the body of the wearer to absorb and contain the various exudates discharged from the body.

Figure 2:
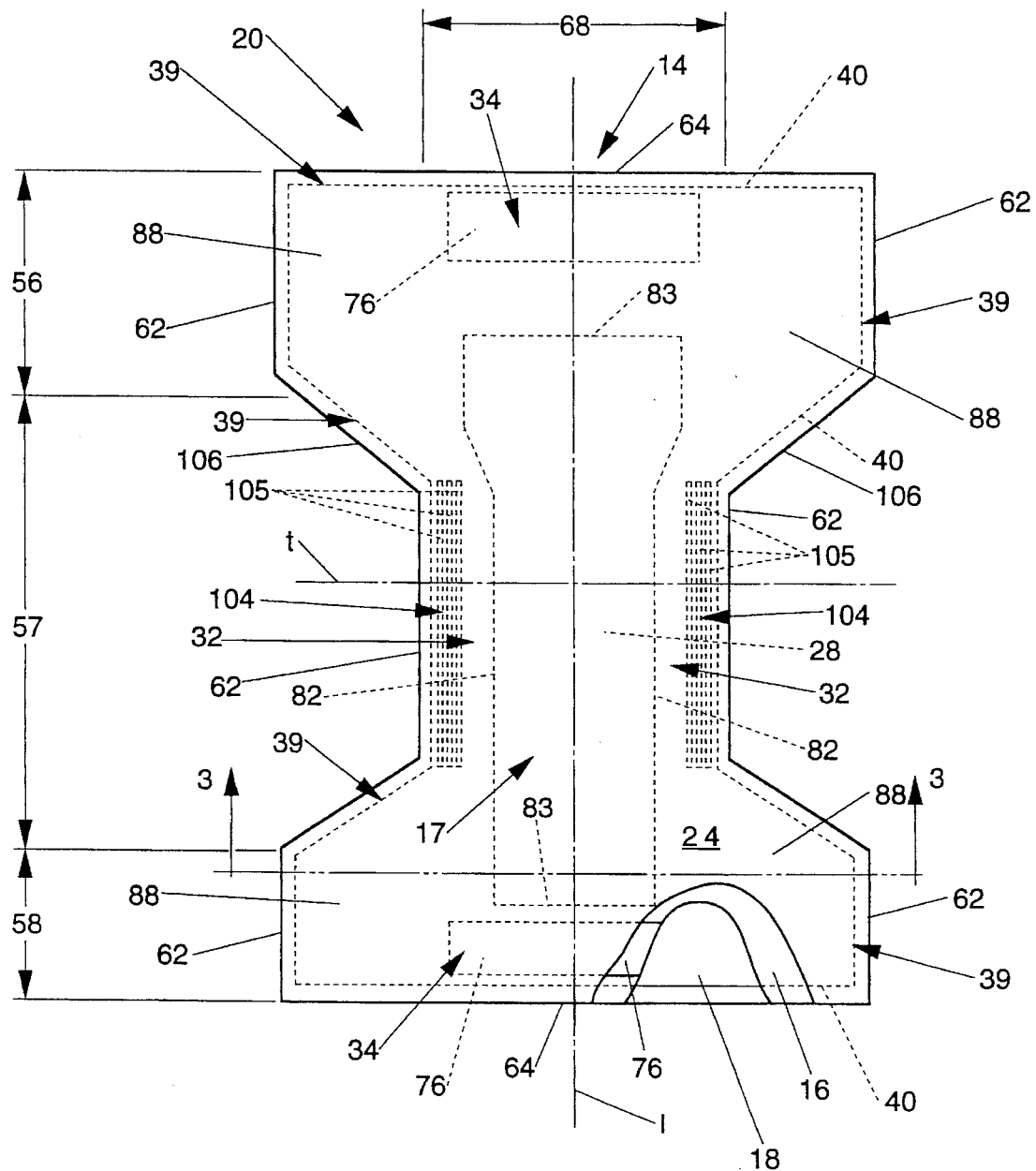
FIG. 2 is a top plan view of the chassis of the training pant embodiment of the present invention having portions cut away to reveal the underlying structure, the surface which will form the outer surface of the disposable absorbent article facing away from the viewer.

A preferred embodiment of the disposable absorbent article of the present invention, disposable training pants 20, is shown in FIG. 1. The training pants 20 of FIG. 1, basically comprise a chassis 14 comprising an inner layer 16 and an outer layer 18; an absorbent assembly 22 comprising at least an absorbent core 28, joined to the inner layer 16 of the chassis 14; and a pair of side seams 10. Referring to FIG. 2, the chassis 14 comprises an inner layer 16 and an outer layer 18 which is joined to the inner layer 16 such that the outer layer 18 will be bloused. The outer layer 18 has a pattern or insignia 15 printed thereon. The printed pattern or insignia 15 of the outer cover 18 tends to draw the viewer's attention away from the underlying inner cover 16 and thereby masks or hides the absorbent core (or the outline of the absorbent core) which is bonded directly or indirectly to the inner layer 16.

As used herein, the term "bloused" shall be understood to mean that portions of a first layer of material are unattached and loosely fitted to a second layer of material, i.e., portions of the first layer of material hang or have been caused to hang loose and full from the second layer of material to which the first layer is joined. As used herein, the term "joined" encompasses configurations whereby an element is directly secured to another element by affixing the element directly to the other element, and configurations whereby the element is indirectly secured to the other element by affixing the element to intermediate member(s) which in turn are affixed to the other element.

In a particularly preferred embodiment, the chassis 14 also comprises elastic waistband members 76, and elastic strands 105 secured to at least the inner layer 16. FIG. 2 is a partially cut-away perspective view of the disposable absorbent article 20 of FIG. 1, prior to the front portion 56 and rear portion 58 of the chassis 14 being secured together by the side seams 10. FIG. 2 shows the chassis 14 in its flat-out, uncontracted state, i.e., with all elastic contraction pulled out of the elastic waistband members 76 and the elastic strands 105 of the elastic legbands 34. The chassis 14 of the present invention preferably has a modified hour-glass shape and is symmetric about the longitudinal centerline 1. The chassis 14 will have at least a front portion 56, a rear portion 58, and a crotch portion 57.

CHASSIS

The inner layer 16 of the chassis 14 is compliant, soft feeling, and non-irritating to the wearer's skin. A suitable inner layer 16 may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers, or composite materials such as a film-coated nonwoven material. Preferably, for the embodiment shown in FIGS. 2 and 3, the inner layer of the chassis is a polymeric film having a thickness of from about 0.012 mm (0.01 mil) to about 0.051 mm (2.0 mils).

In an alternate embodiment, the inner layer 16 may comprise an elastomeric laminate comprising an outer lamina, an inner lamina, and an elastomeric lamina joined between the inner and outer laminae. The inner and outer laminae are joined to the elastomeric lamina while the elastomeric lamina is in a laterally stretched condition such that the contractive forces of the chassis are oriented in the cross machine direction or perpendicular to the longitudinal centerline 1 of the chassis. Such a laminated chassis and methods of forming such a laminated chassis, are disclosed in commonly assigned, co-pending U.S. patent application Ser. No. 08/176,056 (P&G Case 5126), entitled "Elastomeric Disposable Absorbent Article And Method of Making Same" which is being filed concurrently herewith in the name of Patrick J. Allen, et al., and which is incorporated herein by reference.

The outer layer 18 is that portion of the chassis 14 which will form the exterior of the chassis 14, i.e. face away from the wearer. The outer layer 18 is compliant, soft feeling, and non-irritating to the wearer's skin. A suitable outer layer 18 may be manufactured from a wide range of materials, such as plastic films; or woven or non-woven webs of natural fibers (e.g. wood or cotton fibers), synthetic fibers (e.g. polyester or polypropylene fibers), a combination of natural and synthetic fibers, or composite materials such as a film-coated nonwoven material. The outer layer 18 of the chassis 14 may also comprise a composite material having two or more layers, wherein one or all of the layers are bloused from the inner layer 16. Thus, the outer layer 18 could comprise two or more layers of a nonwoven material, or could comprise two or more film layers, or could comprise both nonwoven and film layers. Preferably, the outer layer 18 is a carded nonwoven web of polypropylene fibers. A suitable outer layer is SPN 290 available from Fiberweb North America of Simpsonville, S.C.

Preferably, the outer layer 18 will have a basis weight of about 20 grams per square meter to about 40 grams per square meter. More preferably, the outer layer 18 will have a basis weight of about 25 grams per square meter to about 35 grams per square meter. in a preferred embodiment, the outer layer will have a basis weight of about 30 grams per square meter.

Blousing of the outer layer 18 may be accomplished by providing an oversized outer layer 18 and joining at least a portion of the periphery of the oversized outer layer 18 along at least a portion of the periphery of the inner layer 16. As used herein, the term "oversized outer layer" will refer to an outer layer which is longer (longitudinally) and/or wider (laterally) than the inner layer 16. If the absorbent article of the present invention is being produced on an automated diaper converter which converts webs of material into individual diapers, the bloused outer layer 18 can be formed by feeding the web of outer layer material into the converter at a rate greater than the rate at which the web of inner layer material is fed into the converter, i.e., overfeeding the web of outer layer material.

The outer layer 18 will also have a decorative pattern or insignia 15 printed on the surface thereof. Preferably, the pattern or insignia 15 will be printed on the outer surface. The decorative insignia 15 will tend to draw the viewer's attention from the underlying inner layer 16 and thereby will mask or hide the absorbent core 28 which is joined to the inner layer 16 as discussed herein. The decorative insignia will preferably be a repeating pattern. Examples of suitable decorative insignia would include a repeating pattern of ships, anchors, vehicles, bows, dinosaurs, teddy-bears, animals, flowers, or the like.

The outer layer 18 of the chassis 14 is positioned adjacent to the inner layer 16 and is intermittently or partially joined thereto by attachment means 40 such as those well known in the art. For example, the outer layer 18 may be secured to the inner layer 16 by a uniform continuous layer of adhesive, a patterned layer of adhesive, or an array of separate lines, spirals or spots of adhesive. Adhesives which have been found to be satisfactory are manufactured by Findley Adhesives of Elm Grove, Wis. and marketed as Findley 2031. Alternatively, the attachment means may comprise heat bonds, pressure bonds, ultrasonic bonds, dynamic mechanical bonds, or any other suitable attachment means or combinations of these attachment means as are known in the art. In a preferred embodiment of the present invention, the inner layer and the outer layer are directly joined along the mutually facing surfaces of their peripheral areas 39. As used herein, the "periphery" or "peripheral area" of an element, shall refer to the region, area, or zone adjacent the boundary edges of that element.

The outer layer 18 will be intermittently or partially joined to the inner layer 16 such that at least portions of the common central areas 17 of the inner layer 16 and the outer layer 18 are unadhered together and freely moveable relative to one another. As used herein, the term "central area" shall refer to the area of a material inboard of the periphery, or peripheral area, of that material. The location of the predetermined bonding areas 39 depends on the particular size and shape of absorbent article. FIG. 3 shows attachment means, bond lines 40, that intermittently join together the peripheral areas of the inner layer 16 and the outer layer 18. Thus, the mutually facing surfaces of the inner layer 16 and outer layer 18 that lie laterally inwardly of the bond lines 40 (i.e., central area 17), are substantially free to move relative to each other.

It is not necessary that the peripheral area of the outer layer be entirely bonded to the peripheral area of the inner layer. It is only necessary that the outer layer be sufficiently bonded to the inner layer such that the outer layer is held securely to the absorbent article. It is also not necessary that the entire central area 17 of the outer layer be detached from the inner layer, i.e., it is possible to have the bloused outer cover 18 intermittently joined to the inner layer 16 in the central areas 17 provided portions of the central areas 17 are detached and bloused. The intermittent bonding may be accomplished by spot bonding using ultrasonics, heat seals, or the like, or intermittently bonding using an adhesive pattern of dots or the like.

The bonded or joined surface area between the inner layer 16 and the outer layer 18 is preferably between about 10% to about 50% of the mutually facing surface area between the inner layer 16 and the outer layer 18. More preferably, the bonded or joined surface area between the inner layer 16 and the outer layer 18 is preferably between about 20% to about 30% of the mutually facing surface area between the inner layer 16 and the outer layer 18. In a particularly preferred embodiment, the bonded or joined surface area between the inner layer 16 and the outer layer 18 is preferably about 25% of the mutually facing surface area between the inner layer 16 and the outer layer 18.

The combination of blousing the outer layer such that it hangs loose from the inner layer, and printing the outer layer such that a viewers attention is drawn away from the inner layer, results in the absorbent core (or the outline of the absorbent core) being substantially masked or hidden from the viewer and results in a more garment-like disposable absorbent article.

The chassis 14 of the disposable training pants 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the absorbent article. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise at least a side flap 104 with one or more elastic strands 105. Referring to FIG. 2, leg elastics 105 are preferably positioned between the topsheet 24 and the inner layer 16 of the chassis 14. Alternatively, the leg elastics 105 may be positioned between the inner layer 16 and the outer layer 18 of the chassis 14

The chassis 14 of the disposable training pants 20 further preferably comprises an elasticized waistband 34 disposed adjacent the end edge 64 of the disposable training pants 20 in at least the rear portion 58, and more preferably has an elasticized waistband 34 disposed in both the front portion 56 and the rear portion 58. The waistband of the disposable training pants 20 is that portion which is intended to be placed adjacent the wearer's waist. The elasticized waistband 34 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. Thus, the waistband is generally that portion of the disposable training pants 20 extending from the end edge 64 of the disposable training pants 20 to at least the waist edge 83 of the absorbent core 28. While the elasticized waistband 34 can comprise a separate element affixed to the chassis 14 of the disposable training pants 20, the waistband is preferably an extension of other elements of the disposable training pants 20 such as the topsheet 24, the inner layer 16, or the outer layer 18, or any combination of these elements and an elastomeric material joined thereto. Alternatively, the topsheet 24 and the backsheet 26 of the absorbent assembly 22, may extend beyond the edges of the absorbent core 28 and have an elastomeric material joined thereto to form an elasticized waistband. Disposable training-pants are often constructed so as to have two elasticized waistbands; one positioned in the front portion 56 and one positioned in the rear portion 58. The disposable training pants 20 at least has an elasticized waistband 34 disposed in at least the central region 68 of the rear portion 58. Preferably, as shown in FIG. 2, another elasticized waistband is disposed in the front portion 56.

The elasticized waistband 34 may be constructed in a number of different configurations. In a preferred embodiment of the present invention shown in FIG. 2, the elasticized waistband 34 comprises an elastic waistband member 76 interposed between the topsheet 24 and the inner layer 16 of the chassis 14 and operatively associated therewith to gather the front portion 56 and rear portion 58 of the disposable training pants 20. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference.

Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates (as described in U.S. Pat. No. 5,246,433 which issued to M. H. Hasse, S. W. Miller, and R. P. Bridges on Sep. 21, 1993, which is incorporated herein by reference) or mechanically stretched pretensioned stretch laminates; and elastic strands made from rubber, LYCRA, or other materials. In a preferred embodiment, the elastic waistband member 76 comprises a heat shrinkable elastomeric film.

ABSORBENT ASSEMBLY

The training pants 20 will also comprise an absorbent assembly 22 comprising at least an absorbent core 28 joined to the inner layer 16. The absorbent assembly 22 of the disposable training pants 20, as shown in FIG. 3, may comprise a liquid pervious topsheet 24 joined to the inner layer 16 and an absorbent core 28 positioned between the topsheet 24 and the inner layer 16. In an alternate embodiment of the present invention, shown in FIG. 4, the absorbent assembly 22 may be an insert comprising a liquid pervious topsheet, a liquid impervious backsheet joined to the topsheet, and an absorbent core positioned between the topsheet and the backsheet.

The absorbent core 28 of the absorbent assembly 22, may be any absorbent means which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the disposable absorbent article 20. Further, the size and absorbent capacity of the absorbent core 28 may be varied to accommodate wearers ranging from infants through adults.

A preferred embodiment of the absorbent assembly 22 has a modified hour glass-shape absorbent core 28 which is symmetric about the longitudinal centerline 1. While a preferred embodiment of the absorbent assembly 22 has a modified hourglass-shaped absorbent core 28, it should be understood that the size, shape, configuration and total absorbent capacity of the absorbent core 28 may be varied to accommodate wearers ranging from infants to adults. Therefore, the dimensions, shape and configuration of the absorbent core may be varied (e.g., the absorbent core may have a varying caliper, or a hydrophilic radiant, or may or may not contain absorbent gelling materials). An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. Each of these references are incorporated herein by reference.

The absorbent core 28 is preferably a batt of airfelt and particles of absorbent gelling material, about 13 centimeters wide (lateral dimension), about 37 centimeters long (longitudinal dimension) and approximately 8 centimeters across the narrowest part of the crotch portion 57. Preferably, the portion of the absorbent core that will be generally located in the front portion 56 and crotch portion 57 will have a higher basis weight than the portion of the absorbent core that will be generally located in the rear portion 58. More preferably, the portion of the absorbent core that will be generally located in the front portion 56 and crotch portion 57 will have a basis weight three times the basis weight of the portion of the absorbent core that will be generally located in the rear portion 58. In a preferred embodiment of the absorbent core 28, about 25 centimeters of the absorbent core's length will be generally located in the front portion 56 and crotch portion 57 and will have a basis weight of about 0.96 grams per square inch, and 11 centimeters of the absorbent core's length will be generally located in the rear portion 58 and will have a basis weight of about 0.28 grams per square inch.

Referring to FIG. 3, the absorbent assembly 22 preferably also comprises a liquid pervious topsheet 24 which is joined to the inner layer 16 of the chassis such that the absorbent core 28 is positioned between the topsheet 24 and the inner layer 16. The absorbent core 28 has a garment surface 100, a body surface 101, side edges 82 and end edges 83. The inner layer 16 of the chassis 14 is positioned adjacent the garment surface 100 of the absorbent core 28 and is joined thereto by attachment means (not shown) such as those well known in the art. For example, the inner layer 16 of the chassis 14 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Preferably the inner layer 16 is impervious to liquids and is manufactured from a thin plastic film, although other flexible liquid impervious materials may also be used. As used herein, the term "flexible" refers to materials which are compliant and will readily conform to the general shape and contours of the human body. The liquid impervious inner layer 16 prevents the exudates absorbed and contained in the absorbent core 28 from wetting articles, such as bed sheets and garments, which contact the disposable training pants 20.

The topsheet 24 of the absorbent article 20 is positioned adjacent the body surface 101 of the absorbent core 28 and is preferably joined thereto and to the inner layer 16 by attachment means (not shown) such as those well known in the art. Suitable attachment means are described herein with respect to joining the inner layer 16 to the absorbent core 28. In a preferred embodiment of the present invention, the topsheet 24 and the inner layer 16 are joined directly to each other in the areas extending beyond the absorbent core 28 and are indirectly joined together by directly joining them to the absorbent core 28 by the attachment means (not shown).

The topsheet 24 is that portion of the chassis 14 which will form the interior of the disposable training pants 20, and will contact at least the waist and legs of the wearer. The topsheet 24 of the absorbent article 20 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of hydrophilic material comprising about 20% to 30% rayon so as to feel wet and signal a discharge of urine to a toilet training child.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A suitable topsheet is manufactured by Fiberweb North America of Simpsonville, S.C. and is available as FPN 286.

In an alternate embodiment, shown in FIG. 4, the absorbent assembly 22 may be an insert, i.e., an element formed separately from the chassis and inserted therein. The absorbent insert comprises a topsheet 24, a liquid impervious backsheet 26 joined to the inner layer 16, and an absorbent core 28 positioned between the topsheet 24 and the backsheet 26.

Referring to FIG. 4, the absorbent core 28 and the liquid pervious topsheet 24 may be substantially the same as those described above. The backsheet will be impervious to liquids and will preferably be manufactured from a thin plastic film, although other flexible liquid impervious materials may also be used. The liquid impervious backsheet 26 prevents the exudates absorbed and contained in the absorbent core 28 from wetting articles, such as bed sheets and garments, which contact the disposable training pants 20. The liquid impervious backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

The size of the backsheet 26 is dictated by the size of the absorbent core 28 and the exact disposable garment design selected. In a preferred embodiment, the backsheet 26 will wrap around at least the absorbent core and possibly over the edge portions of the topsheet 24 in at least the crotch portion 57, so that the elasticized leg cuffs 32 will be free from any backsheet material, and, thus, are not inhibited by the backsheet material. Alternatively, the topsheet 24 may wrap around the core and under the edge portions of the backsheet 26 in at least the crotch portion 57, or the topsheet 24 and the backsheet 26 may be "side-notched" in the crotch portion 57 so that the elasticized leg cuffs 32 are not inhibited by the backsheet material.

The backsheet 26 will be joined to the inner layer 16 of the chassis 14 by any means well known in the art. Suitable means of joining the backsheet of the absorbent insert to the inner layer 16 are discussed herein with respect to joining the absorbent core 28 to the inner layer 16.

SIDE SEAMS

The side seams 10 of the chassis 14 may be formed by any means well known in the art. For example, the seams may be sewn, adhesively bonded, ultrasonically bonded, heat sealed, or the like. Suitable methods of forming side seams on disposable absorbent articles, such as training pant, are discussed in U.S. Pat. No. 4,205,679 issued to Repke, et al.; U.S. Pat. No. 4,335,425 issued to Jones, et al.; U.S. Pat. No. 4,610,680 issued to LaFleur, et al.; U.S. Pat. No. 4,619,649 issued to Roberts.; U.S. Pat. No. 4,747,846 issued to Boland, et al.; U.S. Pat. No. 4,641,381 which issued to Heran, et al.; U.S. Pat. No. 4,610,681 issued to Strohbeen, et al.; U.S. Pat. No. 4,909,804 issued to Douglas, Sr.; and U.S. Pat. No. 5,236,430 issued to Russell P. Bridges; which patents are incorporated herein by reference.

In a preferred embodiment of the present invention, the side seams are formed by folding the chassis in the crotch portion 57 so that the longitudinal side regions 88 of the front portion 56 are substantially superposed with the longitudinal side regions 88 of the rear portion 58 forming two seaming areas. As used herein, the term "superpose" will mean to place or set over or above something else such that all like parts substantially coincide. The seam 10 is then formed by any of the means well known in the art. Preferably, the seam is formed by applying pressure and/or heat to the seaming area to effect a bond between the longitudinal side regions of the front portion 56 and the longitudinal side regions 88 of the rear portion 58. Methods of using pressure and/or heat to form a bond between two or more elements, are described in greater detail in U.S. Pat. No. 4,854,984, which issued to Ball et al. on Aug. 8, 1989 which is incorporated herein by reference.

Although the seams of the disposable article of the present invention have been shown and described herein as being fixed seams, i.e., non-reusable seams, the disposable absorbent article of the present invention may be provided seams which allow the article to be opened and re-closed. Seams which allow disposable absorbent articles to be opened and re-closed are well known in the disposable diaper art. These types of seams generally comprise tape tabs joined thereto to the front portion or rear portion of the article. These tape tabs are provided with an adhesive or mechanical fastening means capable of securing the rear portion and front portion in an overlapping configuration about the lower torso of the wearer, and allow the article to be opened and re-closed. Such fastening systems are described in greater detail in U.S. Pat. No. 3,848,594 issued Nov. 19, 1974 to Buell; U.S. Pat. No. 4,699,622 issued Oct. 13, 1987 to Toussant et al.; and U.S. Pat. No. 4,846,815 issued Jul. 11, 1989 to Scripps; all of which are incorporated herein by reference.

ALTERNATE EMBODIMENTS

An alternate embodiment of the present invention, is shown in cross-section in FIG. 5. This embodiment comprises elasticized ear flaps 30 that are unitary with the chassis 14. The elasticized ear flaps 30 are formed by securing an elastomeric ear flap member 90 to each of the ear flaps 72 of the chassis 14 to form an elastomeric laminate. The elastomeric ear flap member 90 is joined to at least the inner layer 16 of the chassis 14. Preferably, as shown in FIG. 5, the elastomeric laminate is formed by securing the elastomeric ear flap member 90 between the inner layer and a portion of the topsheet 24 of the absorbent assembly 22. Each of the ear flaps are then mechanically stretched such that the ear flap is permanently elongated and the laminate is elastically extensible in the direction of initial stretching, once the initial stretching forces are removed from the laminate. Methods of forming unitary elasticized ear flaps are discussed in greater detail in U.S. Pat. No. 5,246,433, "Elasticized Disposable Training Pant And Method Of Making The Same", which issued to M. H. Hasse, R. P. Bridges, and S. W. Miller on Sep. 21, 1993; and U.S. Pat. No. 5,236,430, "Disposable Training Pant Having Fusion Slit Side Seams", which issued to R. P. Bridges on Aug. 17, 1993; which patents are hereby incorporated herein by reference. Although the absorbent assembly 22 of the absorbent article of FIG. 5 comprises an absorbent core 28 positioned between the topsheet 24 and the inner layer 16, the absorbent assembly 22 may comprises an "absorbent insert" such as is described hereinbefore and shown in FIG. 4.

Other suitable training pant structures (without the bloused and printed outer layer of the present invention) are shown in U.S. Pat. Nos. 4,205,679 to Repke, et al.; 4,610,680 to LaFleur; 4,610,681 to Strohbeen, et al.; 4,641,381 to Heran, et al.; 4,909,804 to Douglas, Sr.; and 4,960,414 to Meyer; all of which patents are incorporated herein by reference.

While particular embodiments of the present invention have been illustrated and described, it would be obvious to those skilled in the art that various other charges and modifications can be made without departing from the spirit and scope of the invention. It is therefore intended to cover in the appended claims all such changes and modifications that are within the scope of this invention.

What is claimed is:

1. A garment-like elasticized disposable garment comprising:
    (a) a chassis having:
        (i) a front portion having an end edge, longitudinal side edges, leg edges, a central region, ear flaps, each said ear flap extending laterally outwardly from said central region to said longitudinal side edges and longitudinally along said central region from said end edge to said leg edge;
        (ii) a rear portion opposed to said front portion, said rear portion having an end edge, longitudinal side edges, leg edges, a central region, ear flaps, each said ear flap extending laterally outwardly from said central region to said longitudinal side edges and longitudinally along said central region from said end edge to said leg edge; and
        (iii) a crotch portion between said front portion and said rear portion;
    said chassis including:
        an inner layer having a front portion, crotch portion, end edges, longitudinal side edges, periphery adjacent to said end edges and said longitudinal side edges, and a central area inboard of said periphery;
        an elastic ear flap member joined to each said ear flap in said rear portion and said front portion and extending longitudinally from said end edge of said ear flap toward said leg edge of said ear flap to form an elastomeric laminate, each said elastomeric laminate being mechanically stretched to form an elasticized ear flap in each said ear flap of said chassis, each said ear flap being unitary with said chassis in that said elasticized ear flap comprises a portion of at least said inner layer;
        an absorbent assembly comprising at least a liquid pervious topsheet joined to said inner layer and an absorbent core positioned between said topsheet and said inner layer;
        an oversized outer layer having a front portion, rear portion, crotch portion, end edges, longitudinal side edges, longitudinal side edges, periphery adjacent to said end edges and said longitudinal side edges, and a central area inboard of said periphery, said outer layer being longer than said inner layer, at least a portion of said periphery of said outer layer being joined to a least a portion of said periphery of said inner layer such that said central area of said outer layer blouses away from said central area and inner layer of selected portions, said outer layer additionally having a pattern primed thereon, such that said inner layer with said absorbent assembly joined thereto is substantially unnoticeable to a viewer due to said pattern and said bloused central area of said outer layer; and
    (b) seams joining said front portion of said chassis to said rear portion of said chassis adjacent said longitudinal side edges so as to form two leg openings and a waist opening substantially encircled by said end edges.

2. The disposable absorbent article of claim 1 wherein about 10% to about 50% of said outer layer is joined to said inner layer.

3. The disposable absorbent article of claim 1 wherein about 20% to about 30% of said outer layer is joined to said inner layer.

4. The disposable absorbent article of claim 1 wherein about 25% of said outer layer is joined to said inner layer.

5. The disposable absorbent article of claim 2 wherein said central area of said outer layer is intermittently bonded to said central area of said inner layer at selected portions.

6. The disposable absorbent article of claim 1 wherein said topsheet comprises about 20% to about 30% rayon fibers.

7. The disposable absorbent article of claim 1 wherein said inner layer comprises a liquid impervious material.

8. The disposable absorbent article of claim 1 wherein said absorbent assembly additionally comprises a liquid impervious backsheet joined to said inner layer, said topsheet is joined to said backsheet, and said absorbent core is positioned between said topsheet and said backsheet.

9. The disposable absorbent article of claim 8 wherein said inner layer comprises a liquid pervious material.

10. The disposable absorbent article of claim 8 wherein said topsheet comprises about 20% to about 30% rayon fibers.

* * * * *

UNITED STATES PATENT AND TRADEMARK OFFICE
CERTIFICATE OF CORRECTION

PATENT NO. : 5,575,782

DATED : November 19, 1996

INVENTOR(S) : MARGARET H. HASSE ET AL.

It is certified that error appears in the above-indentified patent and that said Letters Patent is hereby corrected as shown below:

Column 12, line 24, delete "longitudinal side edges,".
Column 12, line 34, "primed" should read -- printed --.

Signed and Sealed this

Twenty-ninth Day of July, 1997

Attest:

BRUCE LEHMAN

Attesting Officer

Commissioner of Patents and Trademarks